United States Patent
Rosseland

[19]

[11] Patent Number: 6,127,594
[45] Date of Patent: Oct. 3, 2000

[54] ABSORBENT STRUCTURE, AND PRODUCTION OF ABSORBENT STRUCTURE BY MAT FORMATION TOGETHER WITH ADHESIVE-BONDED LAYER

[75] Inventor: Berit Rosseland, Vallda, Sweden

[73] Assignee: SCA Hygiene Products AB, Gothenburg, Sweden

[21] Appl. No.: 09/194,429

[22] PCT Filed: May 23, 1997

[86] PCT No.: PCT/SE97/00850

§ 371 Date: Nov. 25, 1998

§ 102(e) Date: Nov. 25, 1998

[87] PCT Pub. No.: WO97/45083

PCT Pub. Date: Dec. 4, 1997

[30] Foreign Application Priority Data

May 31, 1996 [SE] Sweden .................................. 9602154

[51] Int. Cl.$^7$ ...................................................... A61F 13/15
[52] U.S. Cl. .......................... 604/365; 604/367; 604/374; 604/379; 604/375
[58] Field of Search ..................................... 604/366, 384, 604/365, 367, 374, 375, 379; 128/287; 156/62.2, 62.4, 62.8; 264/109; 428/323, 326

[56] References Cited

U.S. PATENT DOCUMENTS

| | | |
|---|---|---|
| 3,938,522 | 2/1976 | Repke . |
| 4,129,132 | 12/1978 | Butterworth et al. . |
| 4,655,757 | 4/1987 | McFarland et al. ..................... 604/366 |
| 5,356,405 | 10/1994 | Thompson et al. ..................... 604/384 |

FOREIGN PATENT DOCUMENTS

WO 94/10956 5/1994 WIPO .

Primary Examiner—John G. Weiss
Assistant Examiner—Michele Kidwell
Attorney, Agent, or Firm—Young & Thompson

[57] ABSTRACT

Absorbent structure consisting of an absorbent material layer of adhesive-free cellulose fibres and an airlaid material layer of adhesive-bonded cellulose fibres, and a method for producing an absorbent structure which is intended for use in an absorbent article. The layers are bonded together by the adhesive of the airlaid material functioning as a binding material and fibres form the absorbent material layer extending into the airlaid material. In the method, the absorbent material is mat-formed on an airlaid material. Alternatively, the absorbent material is mat-formed an airlaid material is then laid on top of it. After the material layers have been laid together, they are compressed at a temperature in excess of 100° C. During the compression, the adhesive of the airlaid material is softened, and the two layers are bonded together. Some of the fibres from the absorption material also penetrate down into the airlaid material and further connection between the layers is achieved.

19 Claims, 3 Drawing Sheets

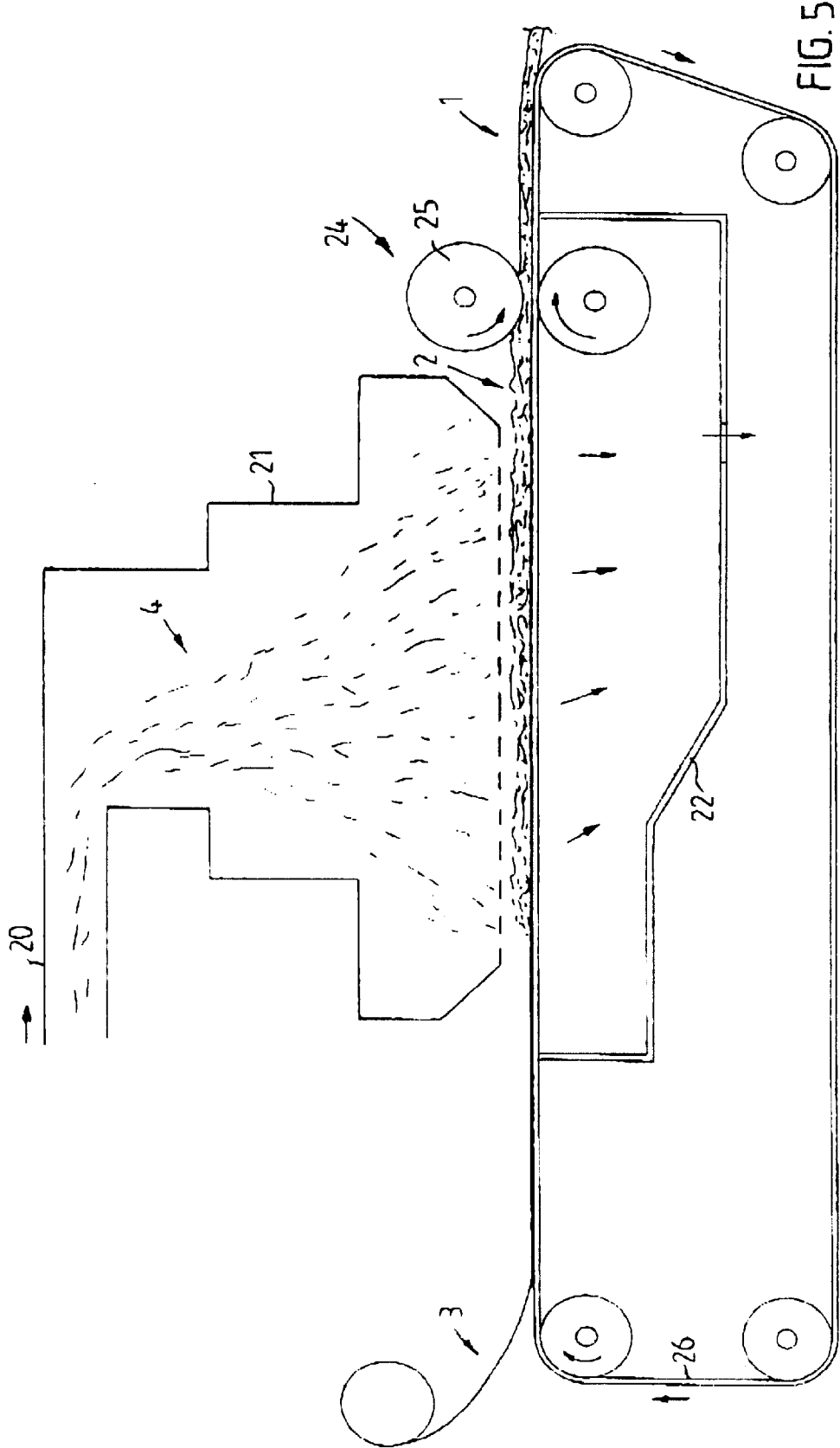

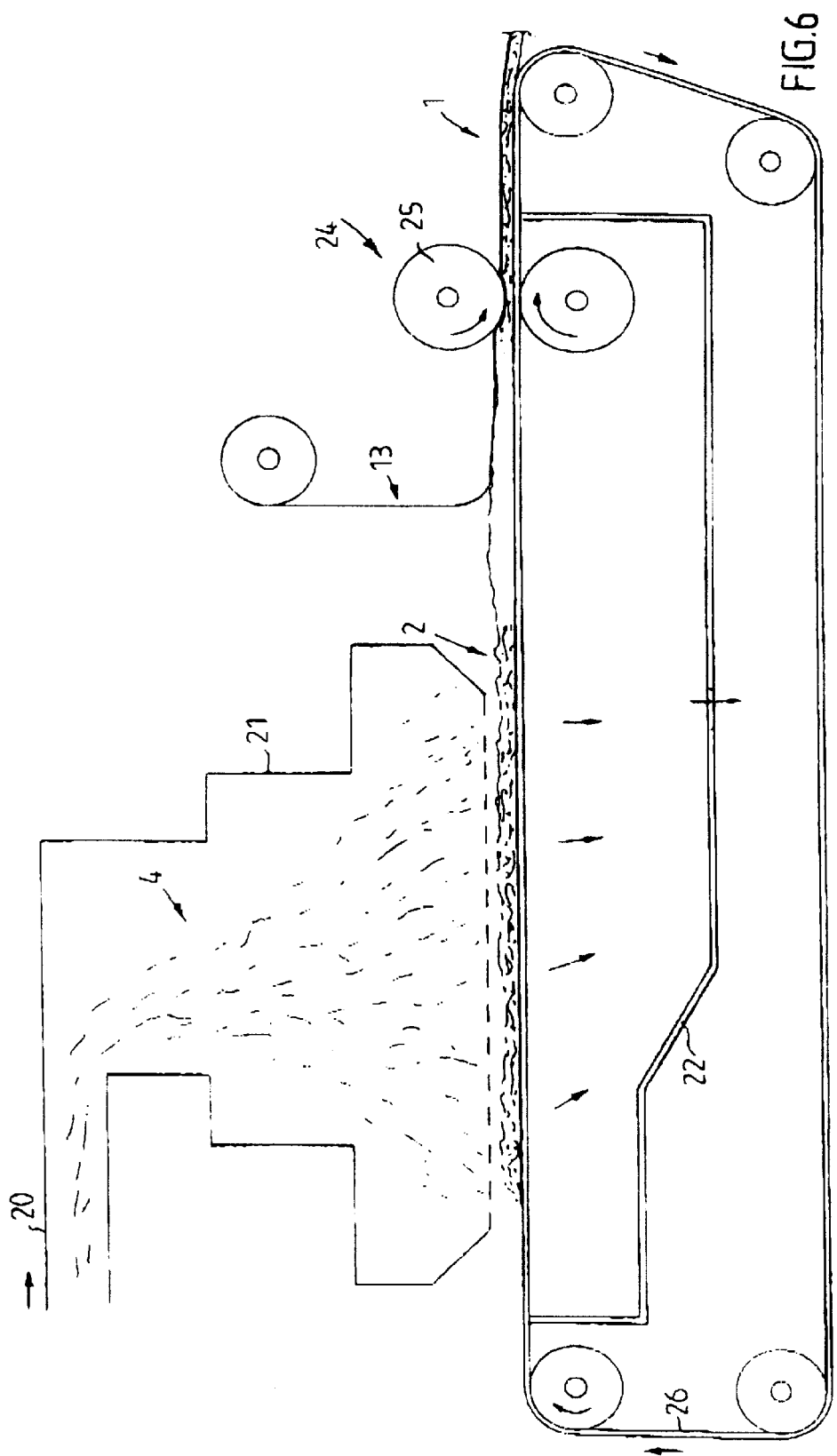

ABSORBENT STRUCTURE, AND PRODUCTION OF ABSORBENT STRUCTURE BY MAT FORMATION TOGETHER WITH ADHESIVE-BONDED LAYER

BACKGROUND

The present invention relates to an absorbent structure consisting of an absorbent material layer and an airlaid material layer, and to a method for producing an absorbent structure which is intended for use in an absorbent article, such as a sanitary towel, panty liner, incontinence pad, diaper, bandage, saliva absorber, or the like.

Absorbent articles of this type are known in a large number of designs. The absorption body in these products can be produced by means of cellulose pulp, for example in rolls, bales or sheets, being dry-defibered and converted in fluffed form to a pulp mat, sometimes with admixture of so-called superabsorbents, which are polymers having the ability to absorb several times their own weight of water or bodily fluid.

The pulp body is often compressed, on the one hand in order to increase its ability to spread liquid, and on the other hand to reduce the bulk of the pulp body and obtain a product which is as compact as possible.

It is of great importance for these products that they have a high absorption capacity, that the total absorption capacity is fully utilized, and that the materials included have a good ability to spread the absorbed liquid. The product should also be thin so that it can be used as discreetly as possible.

SE,B,462 622 describes a readily disintegratable product comprising cellulose-containing fibre material, which product is of such a strength that it can be rolled up or handled in sheet form for storage and transportation, without addition of chemicals which increase the bonding strength between the fibres. Flash-dried fibres of a chemithermomechanical pulp, so-called CTMP, with a dry matter content of about 80%, are formed into a web. The fibres are conveyed by an air stream, in a controlled flow, through a forming head arranged over a wire. The air is sucked off through a suction box arranged under the wire. The web is pre-pressed in order to reduce the web bulk prior to the final pressing to a density of 550–1000 kg/m$^3$. This product is easy to dry-defibre and convert to fluffed form for production of, for example, hygiene articles such as diapers, sanitary towels and similar products. The advantage of the material is that the cellulose pulp in roll form is flash-dried and dry-formed into a web, and the pulp thus has a low content of paper bondings, for which reason the defibering energy is lower than for conventional wet-formed pulp. This also affords possibilities of compressing the material hard, inter alia for reducing the transportation and storage volumes, etc., while retaining the low defibering energy. Another advantage is that superabsorbents can be mixed into the dry-formed material, something which is not possible as regards wet-formed material.

It has been found that this dry-formed material in the non-defibered state is a very good absorption material, and it is possible for the material to be used directly, without defibering, as an absorption material in hygiene articles. This is disclosed in the applications SE 9203445-3 and SE 9203446-1. The material also has good spreading properties and swelling properties. A simpler and less costly production process is achieved, and the conventional defibering and the conventional mat formation are not required. For certain product applications in hygiene articles, it is expedient for dry-formed roll pulp to undergo softening prior to use as absorption material. The good absorption properties and swelling properties already mentioned are not affected to any great extent by the softening process. U.S. Pat. No. 3,938,522 discloses a diaper structure capable of keeping the moisture away from the wearer's skin, which comprises a first layer a porous facing web to be brought into contact with an infant's skin. A second layer, in juxtaposition with the first layer is a highly porous cellulosic batt having greater wettability than the first layer and integral with the second layer is a continuous, paper-like, densified third layer of the same material as the second layer, but of substantially smaller pore size. The third layer is thickened in selected areas providing rapidly drawing away of fluid. A final layer, an impervious sheet, is also provided.

A number of absorbent products, mostly sanitary towels and panty liners which are relatively thin, are nowadays produced using a so-called airlaid material. This material is produced by means of cellulose fibres being airlaid on a wire where they are sprayed with adhesive, for example latex. The airlaid material is thus an adhesive-bonded material. The material is thereafter dried in an oven.

A panty liner consists of a single layer of airlaid material, a lower bottom layer of plastic, for example polyethylene, and an upper surface layer, for example nonwoven. In a sanitary towel the airlaid material is folded into three layers; otherwise, like the panty liner, it consists also of a lower bottom layer made of plastic and an upper surface layer. Other areas of use for the airlaid material are, for example, protective sheets, washing mitts, face cloths, napkins and table cloths.

The previously mentioned dry-formed absorption material is very well suited for use in hygiene products on account of its good absorption properties. In addition, it is without adhesive, which is an advantage from the point of view of cost and the environment. It does, however, have the disadvantage that it is unresilient and brittle and does not hold together so well if the layer of the material is too thin. For producing feminine hygiene products in particular, it is of advantage to have absorption material of narrow web width on a roller or on a spool. In order to supply dry-formed material on narrow rollers (width≈5–10 cm) with the strength which is required, the material has to have a grammage of about 350 g/m$^2$. This grammage is higher than what is in many cases required for the product's function.

The object is the invention is to reduce the grammage of dry-formed absorption material having the strength which is required for it to be supplied on narrow rollers (with≈5–10 cm).

BRIEF DISCLOSURE OF THE INVENTION

In the text which follows we refer to the dry-formed absorption material as the absorption material, and the adhesive-bonded airlaid material is called the airlaid material (see definition in EDANA).

The invention relates on the one hand to an article which is an absorbent structure consisting of an absorbent material layer and an airlaid material layer, and on the other hand to a method for producing an absorbent structure.

The absorbent structure thus consists of an absorbent material layer and an airlaid material layer. The absorbent material consists of adhesive-free cellulose fibres and the airlaid material consists of adhesive-bonded cellulose fibres. The airlaid material layer functions as strengthener and supporter of the absorbent material layer. The various layers adhere to each other by means of the adhesive of the airlaid material functioning as a bonding material. A certain degree of bonding is also achieved by means of fibres from the absorbent material layer extending into the airlaid material layer.

In the method for producing the absorbent structure, the absorption material is used together with the airlaid material, which has good strength and elasticity. The mat formation of the absorption material takes place directly on a previously produced airlaid material. Alternatively, the absorption material is mat-formed on a wire, after which the airlaid material is laid on top of the absorption material. Following the mat formation, the structure is compressed, i.e. the absorption material together with the airlaid material, at a temperature in excess of 100° C., the adhesive of the airlaid material softening and connecting the two layers to each other. Some of the fibres from the absorption material also penetrate down in the airlaid material, and a further connection between the absorption material and the airlaid material is obtained. The airlaid material will function as supporter and strengthening layer for the absorption material. This strengthening and supporting of the absorption material means that thinner absorption material layers can be produced.

DESCRIPTION OF THE FIGURES

FIGS. 5 and 6 show the production of an absorbent structure.

DESCRIPTION OF THE INVENTION

The absorbent structure according to the invention consists of a thin layer of absorption material strengthened and supported by an airlaid material layer. The airlaid material layer is produced by means of cellulose fibres being airlaid on a wire where they are sprayed with adhesive, for example latex, i.e. it is adhesive-bonded. The material is then dried in an oven. The material is white in colour if the cellulose fibres come from bleached chemical pulp, which is customary nowadays. The airlaid material has an elongation of 10–20%, compared with the absorption material which has an elongation of about 1.5%.

Figure 1:
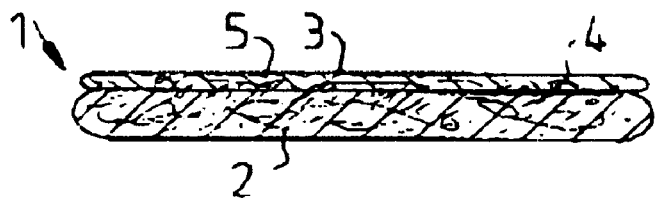
FIG. 1 shows an absorbent structure with an absorbent material layer with an airlaid material layer on top, bonded together by the adhesive of the airlaid material. Some of the fibres of the absorbent material layer penetrate into the airlaid material layer. The figure is not to scale.

The absorbent structure (1) according to the invention, which is shown in FIG. 1, consists of an absorbent material (2) with adhesive-free cellulose fibres (4) and an airlaid material (3) with adhesive-bonded fibres (5). The airlaid material layer (3) is here placed on top of the absorption material layer (2). In one production method, the airlaid material layer will be at the bottom as the absorption material is formed on top of the airlaid material. The airlaid material (3) and the absorption material (2) are bonded to each other by means of the adhesive of the airlaid material (3) fixing the layers together. A certain degree of bonding is also obtained by means of the fibres (4) of the absorption material layer (2) extending into the airlaid material layer (3). The airlaid material (3) functions as a strengthener and supporter of the absorption material (2). The absorbent material has a density of 0.1–1.0 $g/cm^3$, in particular 0.2–0.95 $g/cm^3$, preferably 0.25–0.9 $g/cm^3$, and most preferably 0.3–0.85 $g/cm^3$, and a grammage of 50–250 $g/m^2$, preferably 75–200 $g/m^2$, and most preferably 100–150 $g/m^2$. The airlaid material has a grammage of 30–100 $g/m^2$, preferably 35–80 $g/m^2$, and most preferably 35–50 $g/m^2$. The result is a thin absorption structure with very good absorption properties and with a high level of strength. It has a total grammage of about 85–200 $g/m^2$, in contrast to the previous 350 $g/m^2$ for an absorbent structure consisting of only the absorption material.

The cellulose fibres in the absorption material consist, for example, of flash-dried fibres of chemithermomechanical pulp CTMP. Other examples of fibres which can be used in the absorption material are fibres from thermomechanical pulp CMP, high-temperature thermomechanical pulp HTCTMP, sulphite pulp of kraft pulp.

Figure 2:
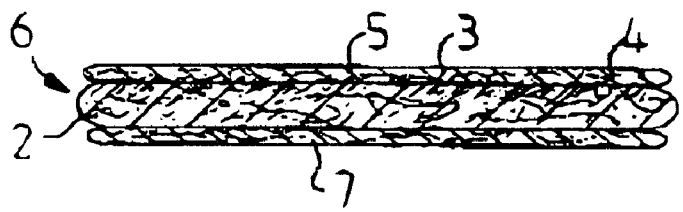
FIG. 2 shows an absorbent structure with an absorbent material layer with two layers of airlaid material, one on top and one at the bottom. These layers too are bonded together by the adhesive of the airlaid material. Some of the fibres of the absorbent material layer penetrate into the upper airlaid material. The figure is not to scale.

Another absorbent structure (6) according to the invention is shown in FIG. 2. In addition to the layers which the structure consists of above in FIG. 1, it has an airlaid material layer (7) under the absorption material layer. The airlaid material has a grammage of 30–100 $g/m^2$, preferably 35–80 $g/m^2$, and most preferably 35–50 $g/m^2$.

The production of the absorbent structure (1) according to the invention is shown in FIG. 5. An absorbent material (2) is mat-formed directly on a layer of airlaid material (3). The airlaid material (3) is laid on a wire (26) and the absorbent material (2) is formed by means of, for example, flash-dried fibres (4) of CTMP being formed into a mat (2) of the absorbent material. The fibres (4) are in this case conveyed by an air stream (20), in a controlled flow, through a forming head (21) arranged over a wire (26). Arranged under the wire (26) there is a suction box (22) which sucks the air off, the CTMP fibres (4) being sucked downwards and some of them penetrating into the airlaid material (3). It is important that the airlaid material (3) is porous and allows air through, since the suction box (22) placed under the wire has to suck off the air transporting the CTMP fibres (4). The mat formation is followed by a compression stage which is carried out at high pressure and with heat. The compression unit (24) consists of two rollers (25) which are at a temperature in excess of 100° C. The latex adhesive is softened and binds the two layers together. As a result of the airlaid material strengthening and supporting the absorption material, it is possible to obtain a thinner absorption structure. Following the compression, the absorbent material has a density of 0.1–1 $g/cm^3$, which gives a thin product with very good absorption properties. A suitable density for the absorbent material is 0.1–1.0 $g/cm^3$, in particular 0.2–0.95 $g/cm^3$, preferably 0.25–0.9 $g/cm^3$, and most preferably 0.3–0.85 $g/cm^3$. It is also possible to add superabsorbents in the stage of mat formation of the absorbent layer.

An alternative procedure according to the invention is shown in FIG. 6. The absorbent material (2) is here mat-formed on the wire (26). The mat formation takes place in the same way as has been described above. The difference from the method described above is that the airlaid material (13) is not laid on the wire, but laid on the absorbent material layer (2) after the actual mat formation, that is to say after the forming head (21) and the suction box (22), but prior to the compression stage in the compression unit (24). The compression takes place at high pressure and with heat, in excess of 100° C. The latex adhesive is softened and binds the two layers together. Here once again the absorbent material is strengthened and supported by the airlaid material. In this case it is not so important for the airlaid material to be porous and have very low grammage, since there will be no air sucked through the airlaid material.

The airlaid material can be produced with a grammage of about 35–50 $g/m^2$. In conjunction with this, it is possible to achieve a grammage for the absorption material which is as low as about 50–150 $g/m^2$, and by means of the strength of the airlaid material a product is obtained which can be supplied on narrow rolls. This gives a total grammage of about 85–200 $g/m^2$, in contrast to the previous 350 $g/m^2$, which was needed for the absorption material alone. The absorbent structure is cut to narrower web widths after production, which is not shown here.

A product having the very good absorption and spreading properties of the absorption material is obtained, while at the same time the material is strengthened through the strength of the airlaid material. It will be thinner than previous dry-formed absorption mats, which is advantageous when it is to be used in sanitary towels and panty liners, for which a low grammage is demanded. However, it can also be used in diapers, for example. Another advantage is that the amount of adhesive is reduced. It is only the thin airlaid material that contains adhesive.

In another alternative production method, two airlaid material layers (3 and 13) can be used together with the absorbent material layer (2). The one layer (3) is laid, as has been described above with reference to FIG. 5, on a wire (26) on which the absorbent material (2) is formed. A further airlaid material layer (13) is laid on top of the absorbent material layer (2) immediately prior to the compression stage (24), this in accordance with the production method in FIG. 6. The production is otherwise carried out as above. This affords a further strengthening of the absorbent structure, and it reduces the fluffing of fibres during production of, for example, panty liners and sanitary towels. In the production of absorbent products, the material will optionally be softened, and troublesome fibre loosening from the absorbent material then occurs. A latex-bonded airlaid material layer does not fluff and therefore functions as a barrier.

The absorption material can also be formed of fibres from thermomechanical pulp CMP, high-temperature thermomechanical pulp HTCTMP, sulphite pulp or kraft pulp.

Where use is not made of the flash-dried CTMP fibres which are formed into a layer, it is possible to form the absorbent material layer by conventional mat formation. In conventional mat formation, pulp in the form of sheets, rolls or bales is dry-defibered or torn. The released fibres in the form of fluff are then blown down in discrete forms or on a web.

In the production of diapers, use is made of discrete forms with perforated bases, the airlaid material layer being placed on the base and the fibres being conveyed down into the form. Mat formation and compression are effected by means of air being sucked out at the base.

There are further advantages of the invention. The absorption material is produced using fibres of a chemithermomechanical pulp, so-called CTMP. Lignin is still present in these fibres, which means that the fibres are hard and have a yellow colour. The airlaid material is white, which gives the absorbent structure a whiter and brighter surface. It can be of advantage for certain products not to have a yellow-coloured surface, since in some cases this may appear unattractive. This also makes it possible to use the absorbent structure as it is, with only the addition of a liquid-impermeable bottom layer.

The airlaid material has an elongation of 10 to 20%, compared to the absorption material which has an elongation of about 1.5%. This greater elongation of the airlaid material makes the airlaid material considerably stronger. It is this strength and flexibility which means that the airlaid material can support and strengthen the dry-formed absorbent material.

An advantage of the dry-formed absorption material is that it is possible to admix superabsorbents therein. As superabsorbents are to be included in the absorbent structure, they are mixed with the absorbent material. The airlaid material then functions as a barrier layer for the superabsorbents, both during the production of an absorbent structure and upon use of an absorbent structure in an absorbent article. During the production, the airlaid material layer lies on the wire under the fibres and the superabsorbents, where they prevent the superabsorbents from being sucked out of the absorbent material layer. Upon use of the absorbent structure, the airlaid material layer can function as a barrier layer if it is placed over the absorbent material layer. The superabsorbents are then prevented from moving out in the direction towards the user when the absorption body together with the superabsorbents has drawn liquid to itself.

For certain product applications in hygiene articles, it is expedient to have the absorbent material undergo softening prior to use as absorption material. The previously mentioned good absorption properties, spreading properties and swelling properties are not affected to any great extent by the softening process. Different softening methods include working between rollers, softening by ultrasound, moistening, or chemical additives.

Illustrative Embodiment

Figure 3:
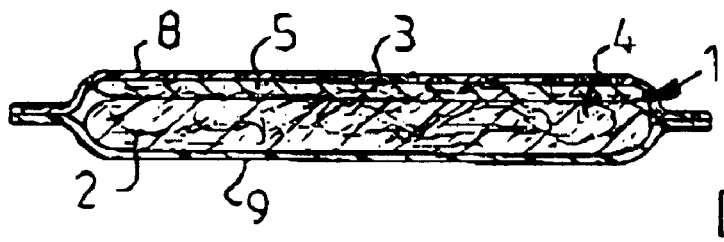
FIGS. 3 and 4 show a diagrammatic layout of an illustrative embodiment with an absorbent structure according to the invention, placed in an article. The figures are not to scale.

FIG. 3 shows an embodiment of an absorbent structure (1) in a sanitary towel. The absorbent structure (1) consists of an airlaid material (3) and an absorbent material layer (2). The airlaid material and the absorbent material are fixed to each other by means of the adhesive of the airlaid material connecting them. A certain connection can also be achieved by means of the fibres (4) of the absorption material extending into the airlaid material. At the top of the article there is a liquid-permeable upper layer (8), for example a nonwoven, which is directed towards the user during use. At the bottom there is a liquid-impermeable bottom layer (9), for example of polyethylene. The layers (8) and (9) have parts which extend beyond the absorbent structure (1) and they are joined to each other in these parts.

Figure 4:
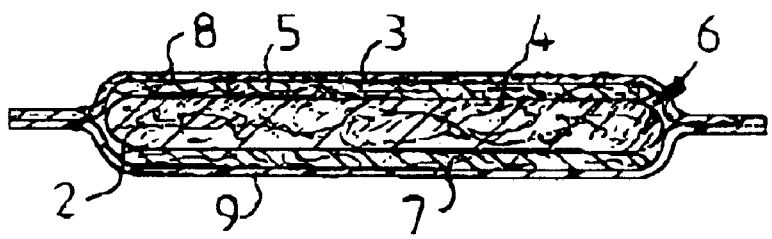

Another illustrative embodiment is shown in FIG. 4 in which the absorbent structure (6) has another airlaid material layer (7) under the absorbent material layer (2) in addition to the airlaid material layer (3) which is placed on top of the absorbent material layer. At the top of the article there is a liquid-permeable upper layer (8), for example a nonwoven, which is directed towards the user during use. At the bottom there is a liquid-impermeable bottom layer (9), for example of polyethylene.

The invention is not limited to the illustrative embodiments shown, and instead is applicable to other embodiments.

What is claimed is:

1. Absorbent structure, for use in an absorbent article, characterized in that it consists of an absorbent material layer of adhesive-free cellulose fibres and at least one airlaid material layer of adhesive-bonded cellulose fibres, the layers being connected to each other.

2. Absorbent structure according to claim 1, characterized in that the airlaid material and the absorbent material are connected to each other by means of the adhesive of the airlaid material.

3. Absorbent structure according to claim 2, characterized in that the airlaid material and the absorbent material are also connected to each other by means of some of the cellulose fibres of the absorption material extending into the airlaid material.

4. Absorbent structure according to claim 2, characterized in that the absorbent material consists of flash-dried fibres of CTMP which have been dry-formed into a layer.

5. Absorbent structure according to claim 4, characterized in that it has a width of about 5–10 cm.

6. Absorbent structure according to claim 5, characterized in that the airlaid material has a grammage of 30–100 g/cm$^2$.

7. Absorbent structure according to claim 6, characterized in that the absorbent material layer has a grammage of 50–250 g/cm$^2$.

8. Absorbent structure according to claim 7, characterized in that the absorbent material has a density of 0.1–1.0 g/cm$^3$.

9. Method for producing an absorbent structure, for use in an absorbent article, characterized in that an absorption material layer of adhesive-free cellulose fibres is laid together with an airlaid material layer of adhesive-bonded cellulose fibres and thereafter compressed.

10. Method according to claim 9, characterized in that the compression takes place at a temperature in excess of 100° C.

11. Method according to claim 10, characterized in that absorption material is mat-formed directly on the airlaid material, with the airlaid material as support.

12. Method according to claim 11, characterized in that the absorption material is mat-formed by means of flash-dried fibres of CTMP being formed into a layer, the fibres being conveyed by an air stream, in a controlled flow, through a forming head arranged over a wire on which the airlaid material layer is placed.

13. Method according to claim 12, characterized in that the arranged under the wire there is a suction box which sucks the air off, the CTMP fibres being sucked downwards and penetrating down into the airlaid material.

14. Method according to claim 10, characterized in that the absorption material is mat-formed on a wire by means of flash-dried fibres of CTMP being formed into a layer, the fibres being conveyed by an air stream, in a controlled flow, through a forming head arranged over a wire, after which an airlaid material is placed on top.

15. Method according to claim 14, characterized in that arranged under the wire there is a suction box which sucks the air off, the CTMP fibres being sucked downwards towards the wire.

16. Method according to claim 13, characterized in that a second airlaid material layer is laid on top of the absorbent material layer prior to the compression stage.

17. Method according to claim 9, characterized in that the airlaid material has a grammage of 30–100 g/m$^2$.

18. Method according to claim 9, characterized in that the absorption material layer is given a grammage of 50–250 g/m$^2$.

19. Absorbent structure according to claim 1 characterized in that the absorbent material layer has a density of 0.1–1.0 g/cm$^3$.

* * * * *